United States Patent [19]

Manome et al.

[11] Patent Number: 4,517,300
[45] Date of Patent: May 14, 1985

[54] PLASMID PSAN 181

[75] Inventors: Taichi Manome; Toshinori Ohmine; Takao Okazaki; Mamoru Arai, all of Hiromachi, Japan

[73] Assignee: Sankyo Company, Limited, Tokyo, Japan

[21] Appl. No.: 475,245

[22] Filed: Mar. 14, 1983

[30] Foreign Application Priority Data

Mar. 16, 1982 [JP] Japan ................................. 57-41227

[51] Int. Cl.³ .................. C12N 1/00; C12N 15/00; C12P 19/34
[52] U.S. Cl. .................. 435/317; 435/172.3; 435/91; 935/29; 935/75
[58] Field of Search .................. 435/317, 172.3, 91

[56] References Cited

U.S. PATENT DOCUMENTS 3,928,569 12/1975 Umezawa et al. ................ 435/128

Primary Examiner—Alvin E. Tanenholtz
Attorney, Agent, or Firm—Frishauf, Holtz, Goodman & Woodward

[57] ABSTRACT

A novel plasmid, named pSAN 181, has a molecular weight of 5±0.2 megadaltons and single cleavage sites for each of the restriction endonucleases BamHI, PstI, XhoI and BglII, the positions of said sites being 0, about 0.85, about 1.15 and about 3.95 megadaltons from the cleavage site of BamHI. The plasmid is extracted from mycelia of microorganisms of the species Streptomyces fulvoviridis, especially the strain Streptomyces fulvoviridis FERM P-6279, and is useful as a vector for genetic engineering.

2 Claims, 1 Drawing Figure

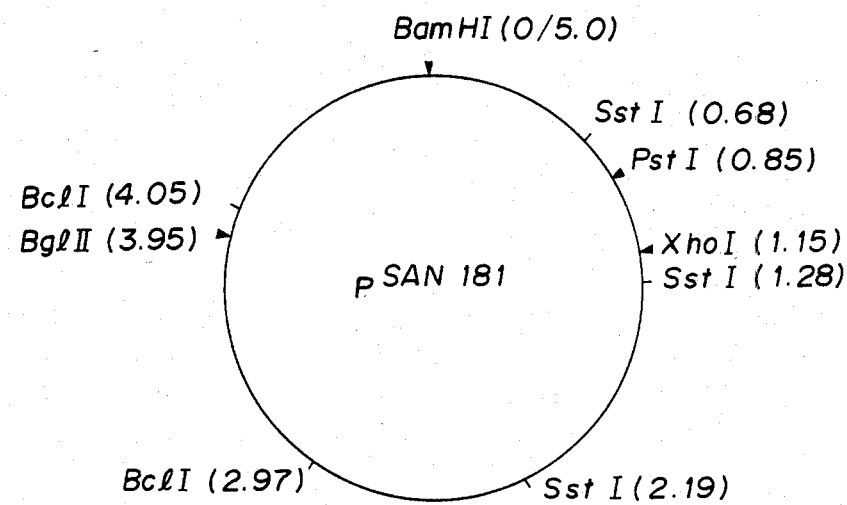

PLASMID PSAN 181

BACKGROUND OF THE INVENTION

The present invention relates to a novel plasmid, which we have named "pSAN 181", and to a process for extracting the plasmid from the mycelia of the species *Streptomyces fulvoviridis*.

Plasmids are autonomously replicating, normally cyclic, double-stranded DNA molecules which do not normally form part of the cellular chromosome and which are believed to carry genetic information which is not essential for the growth of the host cell, whilst the chromosome carries all of the essential genetic information. The plasmids are described as "normally cyclic" as this is the form that they may be seen to adopt in isolation under laboratory conditions; the form adopted under other conditions may or may not be different. The functions in nature of certain plasmids have been discovered, for example, some are known to code for apparatus (e.g. enzymes) providing the host cell with resistance to antibiotics, but many plasmids are "cryptic", i.e. their function in the cell has not been elucidated.

In the field of genetic engineering, however, plasmids are invaluable, in that they provide three different, but related, functions. First they provide a mechanism whereby a selected DNA molecule (generally coding for some valuable function, such as the production of proinsulin or interferon) may be multiplied many times by natural biological activity; this is called "cloning". Second, they provide a mechanism whereby the activity of that DNA molecule may be expressed, i.e. a cell may be induced to produce the material coded for by that DNA molecule by incorporating the genetic information on the plasmid (which includes the added DNA molecule coding for the desired material) into a living cell. Third, they act as transportation vectors to move DNA from one genome to another.

The insertion of a DNA molecule containing desired genetic information into a plasmid is effected by cleaving the plasmid and then splicing the length of added DNA molecule onto each of the free ends of the cleaved plasmid, to reform a larger cyclic DNA molecule, i.e. a larger plasmid. This cleavage is effected by means of an enzyme known as a restriction endonuclease, which catalyses the hydrolysis of the DNA molecule at one or more specific sites. The activity of a particular endonuclease is limited to the catalysis of hydrolysis at a characteristic site and thus causes cleavage of the plasmid at that site. Since the precise nucleotide sequence of many plasmids has not yet been elucidated, plasmids can be identified and characterised by the number and relative separation of the sites on the circular DNA molecular at which various restriction endonucleases cleave the molecule.

To maximise control of genetic engineering work with plasmids, it is desirable that any given restriction endonuclease should cleave the plasmid at a single site only; if the endonuclease cleaves the plasmid at more than one site, a variety of fragments will be formed and these may combine in many different ways. Normally, the smaller the plasmid, the greater will be the chance that a given restriction endonuclease will cleave it at one site only. Ideally, in order to give the greatest possible flexibility, the plasmid will be susceptible to attack by a number of different restriction endonucleases, each capable of cleaving the plasmid at a single characteristic site.

BRIEF SUMMARY OF INVENTION

We have now discovered a plasmid which is remarkably small in comparison with most known plasmids and which has single cleavage sites for four well known and useful restriction endonucleases, specifically those restriction endonucleases known as BamHI, PstI, XhoI and BglII. As is conventional, the novel plasmid is characterised herein by the relative positions of these cleavage sites. For convenience, the cleavage site of BamHI is taken as the origin of the measurements and is therefore given the position 0.

The novel plasmid of the present invention is known as pSAN 181 and which is illustrated in the drawing, has a molecular weight of 5±0.2 megadalton and has single cleavage sites for each of the restriction endonucleases BamHI, PstI, XhoI and BglII, the positions of said sites being 0, about 0.85, about 1.15 and about 3.95 megadaltons, respectively.

The invention also provides a process in which plasmid pSAN 181 is extracted from the mycelia of a microorganism of the species *Streptomyces fulvoviridis*, particularly from a new strain of said species known as SANK 61781 and hereinafter identified by its accession number at the Fermentation Research Institute, Agency of Industrial Science and Technology, Ministry of International Trade and Industry, Ibaraki-ken, Japan, i.e. FERM P-6279. It has also been deposited with the Agricultural Research Culture Collection, Northern Regional Research Centre, Peoria, Ill. U.S. under the accession number NRRL-15308.

DETAILED DESCRIPTION OF INVENTION

The plasmid pSAN 181 has been isolated from the mycelia of a newly identified microorganism strain SANK 61781 belonging to the species *Streptomyces fulvoviridis*.

This microorganism was isolated from a soil sample collected in Fukushima Prefecture, Japan. The morphological and physiological properties of the newly isolated strain were determined using conventional media and the methods described by Shirling and Gottlieb [International Journal of Systematic Bacteriology, 16, 313–314 (1966)], together with several supplementary tests. Observations of the culture were made after incubation at 28° C. for 2 weeks. The colour names and numbers used were assigned according to the "Guide to Colour Standards" (a manual published by Nippon Shikisai Kenkyusho, Tokyo, Japan). The characteristics of the culture were compared with those of various known species of Streptomycetes described in "The Actinomycetes", Volume 2 by Waksman, "The ISP Report" by Shirling and Gottlieb, "Bergey's Manual of Determinative Bacteriology", 8th Edition and other recent literature concerning the taxonomy of the family Streptomycetaceae.

The characteristics of the new strain are summarised as follows:

(1) Morphological characteristics

TABLE 1

| | |
|---|---|
| Branching of hyphae | simple |
| Form of sporophores | straight to curved |
| Surface of spores | smooth |
| Number of spores | 10–50 |

TABLE 1-continued

| | |
|---|---|
| Special organs | none |

(2) Cultural characteristics

TABLE 2

Properties on various plate culture media

| Medium | | |
|---|---|---|
| Yeast-malt agar (ISP 2) | Growth | abundant, pale yellow (6-8-10) |
| | Aerial mycelium | abundant, gray (N-6) |
| | Reverse | dark olive (2-3-12) |
| | Soluble pigment | none |
| Oatmeal agar (ISP 3) | Growth | abundant, pale olive (6-6-10) |
| | Aerial mycelium | abundant, light olive gray (2-8-12) to gray (N-7) |
| | Reverse | pale yellowish brown (8-7-10) to dark olive gray (2-4-11) |
| | Soluble pigment | none |
| Inorganic salt-starch agar (ISP 4) | Growth | moderate, olive gray (1-5-10) |
| | Aerial mycelium | good, brownish white (1-6-6) |
| | Reverse | dark gray (N-3) |
| | Soluble pigment | none |
| Glycerine-asparagine agar (ISP 5) | Growth | good, light olive gray (4-7-11) |
| | Aerial mycelium | good, gray (N-7) |
| | Reverse | olive gray (2-6-11) |
| | Soluble pigment | none |
| Tyrosine agar (ISP 7) | Growth | abundant, olive gray (2-5-11) |
| | Aerial mycelium | abundant, light brownish gray (1-7-10) |
| | Reverse | grayish olive (4-5-11) to dark olive gray (2-3-11) |
| | Soluble pigment | none |
| Sucrose-nitrate agar | Growth | moderate, olive gray (2-6-11) |
| | Aerial mycelium | good, brownish white (1-6-6) |
| | Reverse | olive gray (2-6-11) to dark gray (N-3) |
| | Soluble pigment | none |
| Glucose-asparagine agar | Growth | moderate, grayish olive (4-5-11) |
| | Aerial mycelium | moderate, light olive gray (2-8-11) |
| | Reverse | olive gray (2-5-11) |
| | Soluble pigment | none |
| Nutrient agar (Difco) | Growth | good, yellowish gray (2-9-11) |
| | Aerial mycelium | moderate, grayish white (N-9) |
| | Reverse | yellowish gray (2-9-11) |
| | Soluble pigment | none |
| Potato-carrot extract agar | Growth | moderate, pale yellowish brown (2-7-9) |
| | Aerial mycelium | moderate, light brownish gray (2-7-8) |
| | Reverse | grayish white (N-8) to yellowish brown (4-6-9) |
| | Soluble pigment | none |

(3) Physiological characteristics

TABLE 3

| Physiological tests | |
|---|---|
| Reduction of nitrate | − |
| Hydrolysis of starch | + |
| Liquefaction of gelatin | + |
| Coagulation of milk | − |
| Peptonization of milk | + |
| Melanoid formation | − |
| Decomposition of casein | + |
| Decomposition of tyrosine | − |
| Decomposition of xanthine | + |

For the test of melanoid formation, there were employed three kinds of media: tryptone-yeast extract broth (ISP 1); peptone-yeast extract-iron agar (ISP 6); and tyrosine agar (ISP 7).

(4) Utilization of carbon sources

The medium used was Pridham-Gottlieb agar (ISP 9). The results are shown in Table 4.

TABLE 4

| Carbon sources | |
|---|---|
| D-Glucose | + |
| L-Arabinose | + |
| D-Xylose | + |
| D-Fructose | + |
| L-Rhamnose | + |
| i-Inositol | − |
| D-Galactose | + |
| Sucrose | − |
| β-Galactose | + |
| Raffinose | − |
| D-Mannitol | + |
| Salicin | ± |
| Cellulose | − |
| Control | − |

From the results given above, it can clearly be seen that the new strain belongs to the genus Streptomyces. Of the known species of Streptomyces, this strain most closely resembles *Streptomyces fulvoviridis* (Kuckaeva, Krasil'nikov, Skryabin and Taptykova) Pridham in its morphological, cultural and physiological properties.

Accordingly, the strain has been identified as a strain of *Streptomyces fulvoviridis* and is herein referred to as *Streptomyces fulvoviridis* FERM P-6279.

Cultivation of the chosen strain of *Streptomyces fulvoviridis* can be carried out by conventional methods using culture media containing nutrients well known for use with such microorganisms. Either natural or synthetic culture media may be used, provided that they contain appropriate assimilable carbon sources, assimilable nitrogen sources and suitable inorganic substances. Media which may be used for the cultivation of various species of the genus Streptomyces are very well known in the art and the nature of the medium employed is not critical to the present invention.

Cultivation is preferably effected by a conventional liquid cultivation technique, such as shaking cultivation, under aerobic conditions. The temperature of cultivation is preferably within the range from 18 to 32° C., more preferably from 25° to 30° C. The pH of the culture medium is preferably within the range from 4 to 10, more preferably from 6 to 8. The cultivation time, which may vary depending upon the cultivation conditions, is preferably from 24 to 48 hours, so that the mycelia may be recovered in sufficient amounts.

In order to obtain a satisfactory quantity of mycelia, it is preferred to use proliferated cells, rather than spores, for inoculation. Accordingly, we prefer that spores, from a stored slant culture medium, should first be inoculated onto a nutrient culture base, where they are cultured for a suitable time to give a fresh proliferated cell inoculant. The culture medium employed may be the same as or different from that subsequently used for growth of the microorganism. The fresh proliferated cells are then inoculated aseptically into a culture medium in a suitable vessel, where they are cultured and the microorganism is then collected.

Separation and purification of the plasmid pSAN 181 from the mycelia of Streptomyces fulvoviridis FERM P-6279 may be effected by known methods, for example as disclosed in the Journal of Antibiotics 33, 88–91 (1980). In this method,, the mycelia are suspended in a buffer containing ethylenediaminetetraacetic acid (EDTA). An enzyme capable of dissolving cell walls, for example lysozyme, and preferably a surfactant, such as sodium dodecyl sulphate, are then added to effect lysis. The sodium dodecyl sulphate is precipitated by adding aqueous sodium chloride and removed; ribonuclease and pronase are then added to the supernatant to liberate the DNA. This DNA is then subjected to cesium chloride-ethidium bromide equilibrium density gradient centrifugation to separate the circular DNA of plasmid pSAN 181 from the chromosomal DNA. The plasmid DNA thus separated is collected by a suitable method, the ethidium bromide is removed with butanol, and then the DNA is purified by dialysis. The purified product may be further purified by equilibrium density gradient centrifugation, sucrose density gradient centrifugation or agarose gel electrophoresis, if desired. Plasmid pSAN 181 can also be separated by alkali treatment and isolation as disclosed in Anal. Biochemi. 76, 431–441 (1976).

Plasmid pSAN 181 when thus obtained in pure form was found by electron microscopic observation (using pBR 322 as the internal standard) to have an average contour length of 2.5–2.6 $\mu$m and a molecular weight of 5±0.2 megadaltons. The sensitivity of plasmid pSAN 181 to various restriction endonucleases was examined as follows.

The restriction endonucleases employed were products obtained from New England Biolabs and Bethesda Research Laboratories. Digestion with each restriction endonuclease was carried out using an excess of 2 to 3 times the required amount of enzyme under the digestive conditions specified by the manufacturers. When carrying out digestion using two or more kinds of restriction endonucleases, digestion with the restriction endonuclease requiring the lower ionic strength was carried out first, after which the ionic strength of the reaction mixture was adjusted to that required by the second restriction endonuclease and then the second digestion was carried out.

The digested samples were subjected to agarose gel electrophoresis (using a Slab gel electrophoresis device produced by Ato Co. Ltd., Japan). The digestive sample was placed on a 0.8% or 1.2% by weight agarose gel and electrophoresis was carried out at a constant current of 30–35 mA in a borate buffer (containing 89 mM Tris-hydroxymethylaminomethane, 2.5 mM disodium ethylenediaminetetraacetate and 89 mM boric acid, pH 8.3) for 2.5 to 3 hours to separate the cleaved fragments. The fragments were detected by immersing the gels after electrophoresis in a borate buffer containing ethidium bromide at a concentration of 1 $\mu$g/ml for 10 minutes and photographing the positions of the DNA fragments detected by ultraviolet irradiation at 302 nm.

The molecular weight of plasmid pSAN 181 calculated from the fragments cleaved by the respective restriction endonucleases was in agreement with that obtained by electron microscopy, i.e. 5±0.2 megadaltons. As a marker for measurement of the molecular weight of the cleaved fragments, we used the fragment obtained by digestion of $\lambda$-phage DNA with Hind III or EcoRI.

The measured sensitivities of plasmid pSAN 181 to the respective restriction endonucleases are as shown in Table 5 and a map of the sites of cleavage by the restriction endonucleases is shown in the accompanying drawing. The cleavage sites are designated as distances in magadaltons from the cleavage site of BamHI.

TABLE 5

| Sensitivities of plasmid pSAN 181 to various restriction endonucleases | | |
|---|---|---|
| Restriction endonuclease | Number of cleavages | Cleavage site |
| EcoRI | 0 | — |
| BglII | 1 | 3.95 |
| BamHI | 1 | 0/5.0 |
| XhoI | 1 | 1.15 |
| KpnI | 0 | — |
| XbaI | 0 | — |
| HindIII | 0 | — |
| BclI | 2 | 2.97, 4.05 |
| SstI | 3 | 0.68, 1.28, 2.19 |
| PstI | 1 | 0.85 |

The results reported above are given as averages of the results obtained with different samples of plasmid pSAN 181; thus, for example, fragments obtained on digestion with BglII were all within the range from 3.79 megadaltons (when the measured plasmid length was 4.8 megadaltons) to 4.11 megadaltons (when the measured plasmid length was 5.2 megadaltons).

Plasmid pSAN 181 can be used for the preparation of recombinant DNA which can be introduced by transformation, transduction or conjugation into a host organism. Specifically, the isolated and purified plasmid pSAN 181 can be cleaved at one position by a suitable restriction endonuclease chosen from BamHI, BglII, PstI or XhoI, converting it to a linear DNA molecule having a molecular weight of 5±0.2 megadaltons. A non-vector, exogenous DNA containing a desirable sequence is also cleaved with the same restriction endonuclease and is mixed with the linear DNA derived from plasmid pSAN 181. The free ends ("sticky" ends or "flush" ends) of the non-vector DNA and of the linear plasmid DNA form pairs with each other and are then ligated by covalent bonding using DNA ligase to form a single circular DNA. This procedure can be used for inserting DNA containing desirable genetic information from eucaryotic or procaryotic cells into plasmid pSAN 181. Alternatively, after, if necessary, removing the sticky ends with an exonuclease, new sticky ends may be synthesized in situ using deoxynucleoside polyphosphates, to give, for example, polydA and polydT complementary sequences.

The resulting recombinant circular DNA is then, as is well known, introduced into a microorganism where its activity may be expressed. Examples of eucaryotic cell genes which may be introduced into microorganisms in this way include genes coding for somatostatin or proinsulin, whilst examples of procaryotic cell genes are genes coding for penicillinase or amylase or genes coding for enzymes in the biosynthetic systems of antibiotics. Alternatively, non-coding control sequences may be introduced by similar methods.

The invention is further illustrated by the following non-limiting Example.

EXAMPLE (1) Cultivation of Streptomyces fulvoviridis FERM P-6279

20 ml of a culture medium containing 0.4% w/v glucose, 1.0% w/v malt extract and 0.4% w/v yeast extract was charged into a 50 ml flask having a side arm, and then spores of *Streptomyces fulvoviridis* FERM P-6279 were inoculated into the flask. The microorganism was then cultivated with reciprocal shaking at 120 rpm and 25°-30° C. for about 72 hours.

At the end of this time, the resulting seed culture was inoculated into a 500 ml Sakagucni flask containing 100 ml of a culture medium having the composition given below in an amount corresponding to 1-5% by weight of the culture mediium. The composition of the culture medium was (percentages are w/v):

| | |
|---|---|
| glycerol | 0.4% |
| casamino acid | 0.4% |
| yeast extract | 0.005% |
| malt extract | 0.1% |
| magnesium sulphate | 0.1% |
| calcium carbonate dihydrate | 0.01% |
| monobasic potassium phosphate | 0.2% |
| disodium phosphate dodecahydrate | 0.8% |

Cultivation was carried out with reciprocal shaking at 120 rpm and 25°-30° C. for 24-48 hours.

(2) Isolation and purification of plasmid pSAN 181

Mycelia were collected from the culture broth obtained as described above by low speed centrifugation at 10,000 G and at 4° C. for 20 minutes and the supernatant was removed by decantation to give mycelial pellets. These mycelial pellets were suspended in 20 ml of a TES buffer (containing 25 mM Tris-hydroxymethylaminomethane, 25 mM disodium ethylenediaminetetraacetate and 25 mM sodium chloride, pH 7.5). To the suspension were added 1 ml of a 40 mg/ml lysozyme solution, and the mixture was incubated at 37° C. with gentle shaking for 5-15 minutes. At the end of this time, 3 ml of a 10% w/v aqueous solution of sodium dodecyl sulphate were added and the mixture was incubated with gentle shaking at 37° C. for 5 minutes to complete lysis.

The resulting lysate was centrifuged at 40,000 G and 4° C. for 30 minutes to give a cleared lysate as the supernatant. To this was added one quarter of its volume of 5M aqueous sodium chloride to give a final sodium chloride concentration of 1M. The mixture was then cooled at 0° C. for 2-3 hours, which precipitated the sodium dodecyl sulphate; the precipitate was removed by centrifugation at 3,000 G and 0° C. for 15 minutes.

Ribonuclease was then added to the supernatant and digestion was effected at 37° C. for 20 minutes, after which pronase was added and digestion was carried out again at 37° C. for 20 minutes. At the end of this time, a 40% by weight solution of polyethylene glycol 6,000 was added to a final concentration of 10% by weight and the mixture was maintained at 0° C. overnight, to precipitate the DNA. The mixture was gently centrifuged at 3,000 G and 0° C. for 15 minutes and the supernatant was discarded. The precipitate was suspended in 4.7 ml of a TES buffer in which it partially dissolved; it was then dialysed against a TES buffer to give a DNA extract sample.

This sample was mixed with cesium chloride and then with ethidium bromide, a fluorescent compound, to give a solution having a density of 1.620 g/ml. This solution was subjected to equilibrium density gradient centrifugation at 150,000 G and 18° C. for 40 hours. When the centrifugation tube was irradiated with ultra-violet radiation at 320 nm, the closed circular plasmid DNA was found to have separated as a thin fluorescent band under the strong fluorescent band of the linear chromosomal DNA.

The band containing the closed circular plasmid DNA was collected, extracted three times with equal volumes of butanol to remove the ethidium bromide and then the aqueous layer was dialyzed against a pH 7.5 buffer containing 10 mM Tris-hydroxymethylaminomethane, 10 mM sodium chloride and 1 mM ethylenediaminetetraacetic acid, to give pure plasmid pSAN 181.

The molecular weight of plasmid pSAN 181 was determined by observing its open molecules using electron microscopy, in which the average contour length was observed to be between 2.5 and 2.6 μm, using plasmid pBR 322 as the internal standard.

We claim:

1. Isolated plasmid pSAN 181 having a molecular weight of 5±0.2 megadaltons and having single cleavage sites for each of the restriction endonucleases BamHI, PstI, XhoI and BglII, the positions of said cleavage sites being 0, about 0.85, about 1.15 and about 3.95, and multiple cleavage sites for the restriction endonuclease BclI at about 2.97 and 4.05 and for the restriction endonuclease SstI at about 0.68, 1.28 and 2.19 megadaltons, respectively, from the cleavage site of BamHI.

2. A process for providing an isolated plasmid having a molecular weight of 5±0.2 megadaltons and having single cleavage sites for each of the restriction endonucleases BamHI, PstI, XhoI and BglII, the positions of said sites being 0, about 0.85, about 1.15 and about 3.95, and multiple cleavage sites for the restriction endonuclease BclI at about 2.97 and 4.05 and for the restriction endonuclease SstI at about 0.68, 1.28 and 2.19 megadaltons, respectively from the cleavage site of BamHI cooomprising culturing *Streptomyces fulvoviridis* FERM P-6279 to produce larger amounts of said *Streptomyces fulvoviridis* FERM P-6279 which contain mycelia, separating said mycelia from the culture broth, and isolating said plasmid from said mycelia.

* * * * *